US012589169B2

(12) United States Patent
Chang et al.

(10) Patent No.: US 12,589,169 B2
(45) Date of Patent: Mar. 31, 2026

(54) COMPOUND AND MRI CONTRAST AGENT CONTAINING SAME

(71) Applicant: KYUNGPOOK NATIONAL UNIVERSITY INDUSTRY-ACADEMIC COOPERATION FOUNDATION, Daegu (KR)

(72) Inventors: Yong Min Chang, Daegu (KR); Ah Rum Baek, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 458 days.

(21) Appl. No.: 18/023,360

(22) PCT Filed: Oct. 5, 2021

(86) PCT No.: PCT/KR2021/013576
§ 371 (c)(1),
(2) Date: Feb. 25, 2023

(87) PCT Pub. No.: WO2022/092602
PCT Pub. Date: May 5, 2022

(65) Prior Publication Data

US 2023/0330272 A1 Oct. 19, 2023

(30) Foreign Application Priority Data

Oct. 30, 2020 (KR) ........................ 10-2020-0143616

(51) Int. Cl.
*A61K 49/10* (2006.01)
*C07D 257/02* (2006.01)

(52) U.S. Cl.
CPC .......... *A61K 49/106* (2013.01); *C07D 257/02* (2013.01)

(58) Field of Classification Search
None
See application file for complete search history.

(56) References Cited

FOREIGN PATENT DOCUMENTS

| | | | |
|---|---|---|---|
| KR | 10-2012-0033769 | A | 4/2012 |
| KR | 10-2015-0083721 | A | 7/2015 |
| KR | 10-2019-0111356 | A | 10/2019 |
| WO | 03/009874 | A1 | 2/2003 |
| WO | 03/013617 | A2 | 2/2003 |

*Primary Examiner* — Celeste A Roney
(74) *Attorney, Agent, or Firm* — Goldilocks Zone IP Law

(57) ABSTRACT

The present invention relates to a novel compound and an MRI contrast agent containing same. The compound according to the present invention can minimize MRI contrast agent side effects caused by the release of gadolinium ions within the body, on the basis of the outstanding kinetic stability, and can be very usefully employed as an MRI contrast agent for diagnosing liver diseases, owing to the superior level of contrast enhancement for the liver in an MRI image of the body in comparison with other organs.

9 Claims, 16 Drawing Sheets

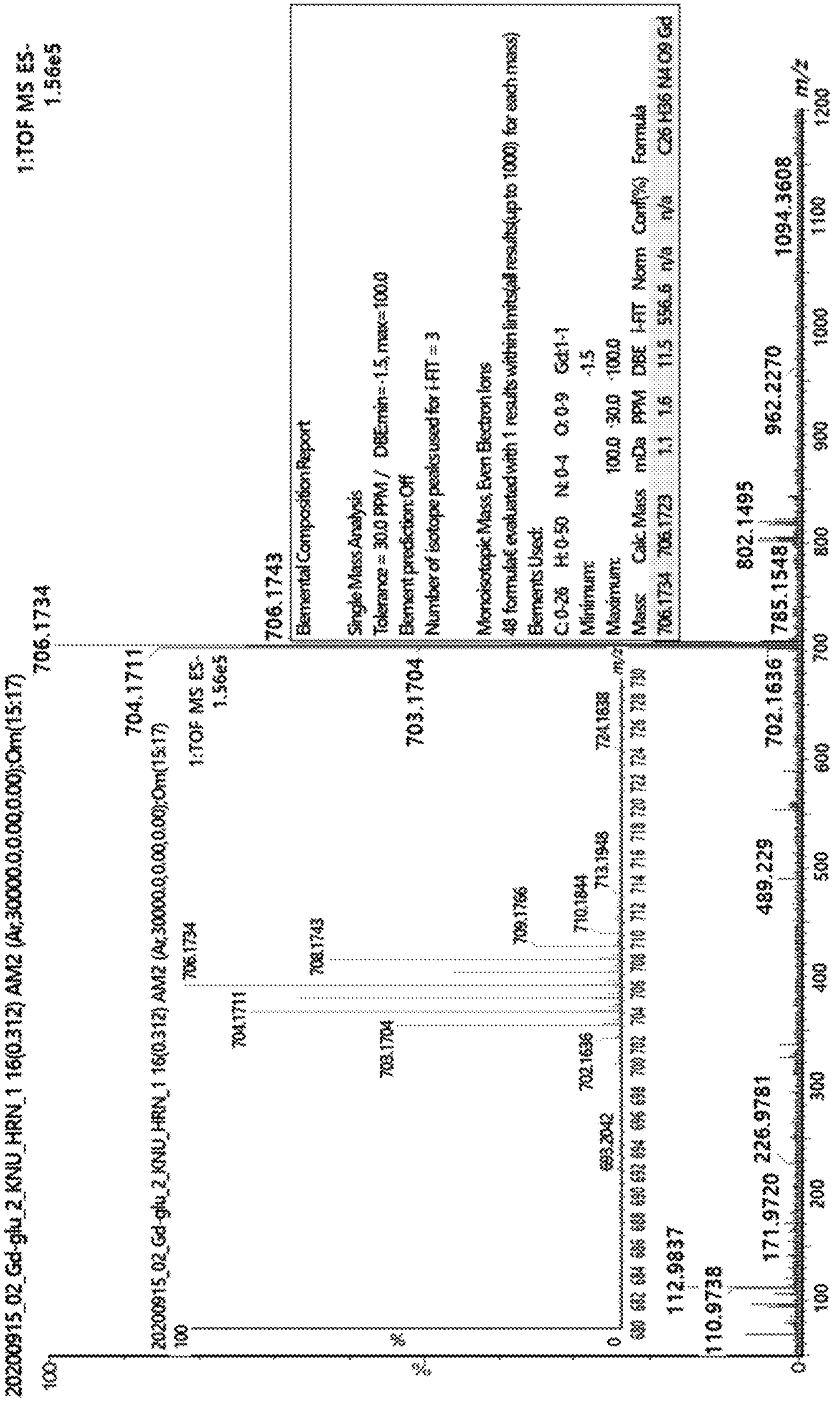

FIG. 10

1:TOF MS ES-
1.56e5

1:TOF MS ES-
1.56e5

202200915_02_Gd-glu_2_KNU_HRN_1_16(0.312) AM2 (Ax,30000.0,0.00,0.00);Cm(15:17)

202200915_02_Gd-glu_2_KNU_HRN_1_16(0.312) AM2 (Ax,30000.0,0.00,0.00);Cm(15:17)

Elemental Composition Report

Single Mass Analysis
Tolerance = 30.0 PPM /   DBE:min=-1.5, max=100.0
Element prediction: Off
Number of isotope peaks used for i-FIT = 3

Monoisotopic Mass, Even Electron Ions
48 formulae evaluated with 1 results within limits(all results(up to 1000) for each mass)
Elements Used:
C: 0-26   H: 0-50   N: 0-4   O: 0-9   Gd:1-1

| Mass | Calc. Mass | mDa | PPM | DBE | i-FIT | Norm | Conf(%) | Formula |
|---|---|---|---|---|---|---|---|---|
| Minimum: | | | | -1.5 | | | | |
| Maximum: | | 100.0 | 30.0 | 100.0 | | | | |
| 706.1734 | 706.1723 | 1.1 | 1.6 | 11.5 | 536.6 | n/a | n/a | C26 H36 N4 O9 Gd |

COMPOUND AND MRI CONTRAST AGENT CONTAINING SAME

CROSS-REFERENCE TO RELATED APPLICATIONS

This application claims the benefit under 35 U.S.C. section 371, of PCT International Application No. PCT/KR2021/013576, filed on Oct. 5, 2021, which claims priority to Korean Patent Application No. 10-2020-0143616, filed on Oct. 30, 2020, in the Korean Intellectual Property Office, both of which are hereby incorporated by reference in their entireties.

TECHNICAL FIELD

The present invention relates to a novel compound and an MRI agent containing the same. Specifically, the present invention relates to a novel compound, which has high in vivo stability and is capable of diagnosing of liver diseases, and an MRI agent containing the same.

BACKGROUND ART

Magnetic resonance imaging (hereinafter, MRI) is a method of obtaining anatomical, physiological, and biochemical information images of the body by using a phenomenon in which the distribution of hydrogen atoms is different between tissues of the body and the hydrogen atoms are relaxed in a magnetic field.

Unlike CT or PET, MRI does not use radiation that is harmful to the human body but creates images inside the body using the gradient of the magnetic field and radio waves under a strong magnetic field; therefore, MRI is non-invasive, has high resolution, and is excellent for examination of soft tissues.

In order to utilize the MRI equipment more precisely, a contrast agent is injected into an object so as to obtain an MRI image. The contrast between tissues on the MRI image is a phenomenon that occurs because the relaxation action of the nuclear spin of water molecules to return to an equilibrium state varies by tissue.

The contrast agent plays the role of further sharpening the contrast between tissues through widening the difference in relaxation rates between tissues by affecting the relaxation action using a paramagnetic or superparamagnetic material and inducing changes in MRI signals.

Currently, the contrast agent most commonly used clinically is a gadolinium (Gd) chelate-based contrast agent. Among them, contrast agents based on a linear chelate structure are being used as a liver-specific MRI contrast agent for use in MRI imaging of microscopic liver cancer and other liver diseases.

However, a commercially available liver-specific MRI contrast agent has low in vivo stability due to its linear chelate structure, and thus there is a possibility of gadolinium ion leakage in the body, which has a problem in that it can be used in a limited manner.

DISCLOSURE

Technical Problem

An object of the present invention is to provide a novel compound having high in vivo stability and capable of diagnosing liver diseases.

Another object of the present invention is to provide an MRI contrast agent containing the compound.

Technical Solution

According to the present invention, there is provided a compound represented by the following Formula 1:

[Formula 1]

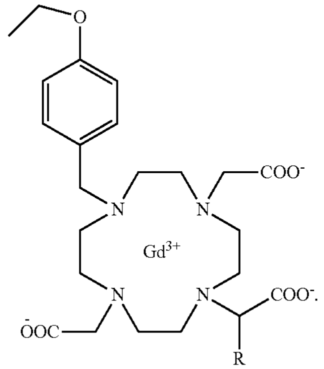

In Formula 1 above,

R represents —COO—, —$CH_2COO$—, or —$CH_2CH_2COO$—.

In an embodiment, Formula 1 above is represented by the following Formula 1-1, 1-2, or 1-3.

[Formula 1-1]

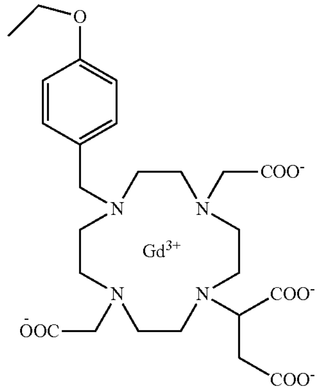

[Formula 1-2]

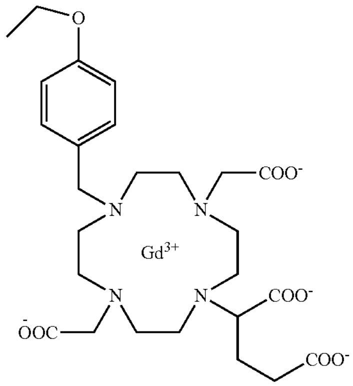

-continued

[Formula 1-3]

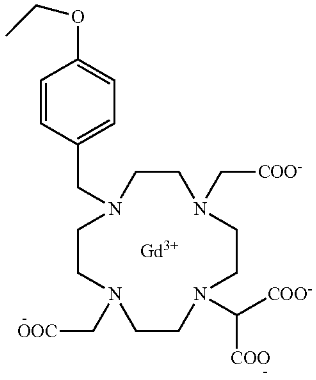

In an embodiment, the compound is characterized in that it specifically binds to liver tissue.

Additionally, according to the present invention, there is provided an MRI contrast agent containing the compound represented by Formula 1 above.

In an embodiment, the MRI contrast agent may be used for the diagnosis of liver diseases, more specifically, diagnosis of cancer liver metastasis, liver cyst, liver cancer, or biliary obstruction.

In an embodiment, the MRI contrast agent is characterized in that it has a magnetic relaxation rate of 5 $mM^{-1}s^{-1}$ to 10 $mM^{-1}s^{-1}$ in the 4.7 T magnetic resonance imaging.

Advantageous Effects

The compound according to the present invention has an appropriate magnetic relaxation rate and has excellent kinetic stability and thus has improved in vivo stability; therefore, when it is used as an MRI contrast agent, side effects of the MRI contrast agent due to the in vivo leakage of gadolinium ions can be minimized.

In addition, the compound according to the present invention has an excellent degree of enhancement of liver contrast compared to other organs in an in vivo MRI image; therefore, it can be very usefully used as an MRI contrast agent for the diagnosis of liver diseases.

BRIEF DESCRIPTION OF DRAWINGS

FIG. 10 shows the results of HR-ESIMS (negative mode) analysis of the (Gd-suc) compound according to Example 2 of the present invention.

MODE FOR CARRYING OUT THE INVENTION

Figure 1:
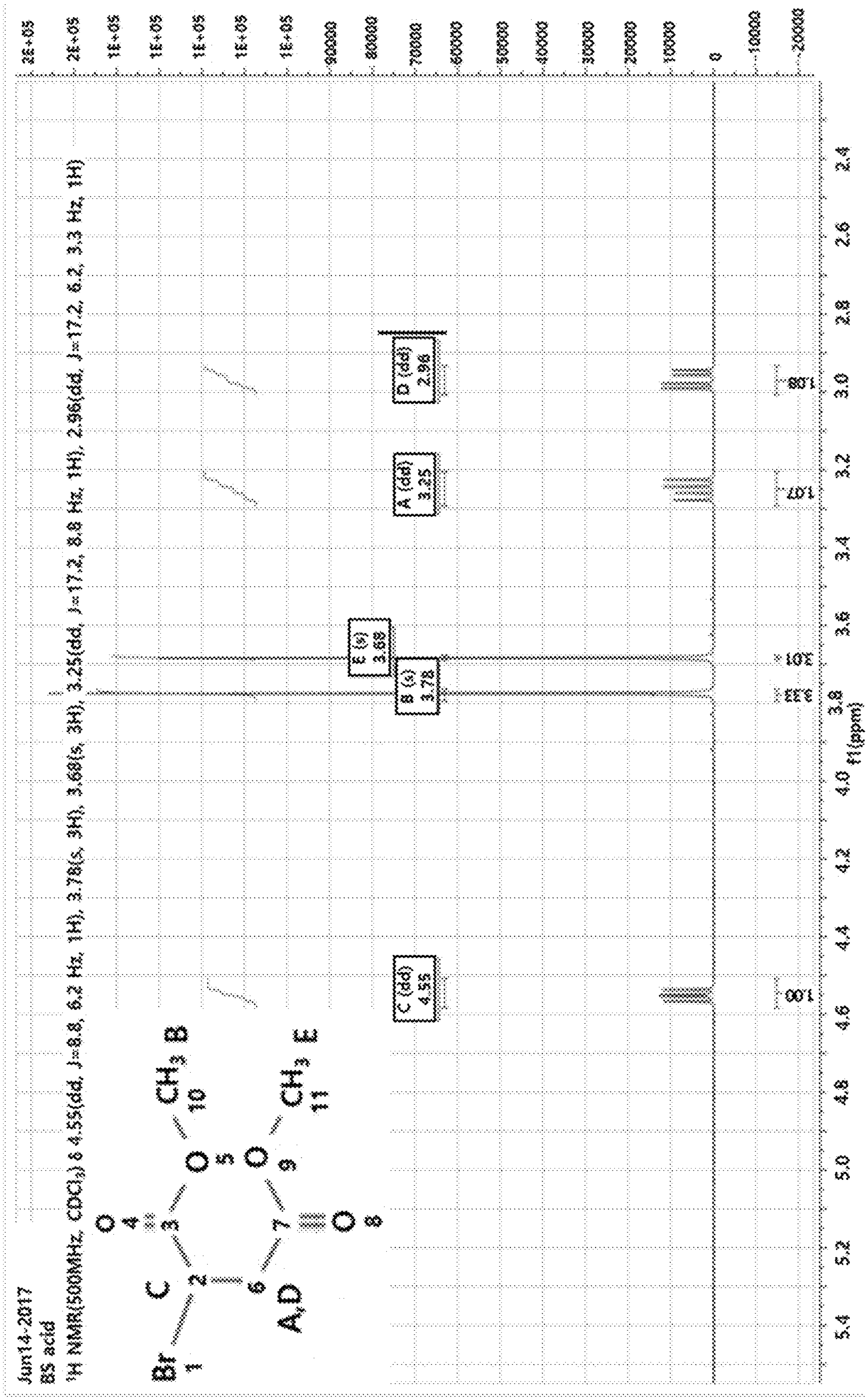
FIG. 1 shows the $^{1}H$ NMR (500 MHz) spectrum of Compound (1) produced during the synthesis of the compound according to the present invention.

Hereinafter, the terms used in the present invention are merely used to describe specific embodiments and are not intended to limit the present invention. Unless defined otherwise, all terms used herein, including technical or scientific terms, have the same meaning as commonly understood by those skilled in the art to which the present invention pertains. Terms such as those defined in commonly used dictionaries should be interpreted as having a meaning consistent with the meaning in the context of the related art, and should not be interpreted in an ideal or excessively formal meaning unless explicitly defined in the present invention.

The compound according to an embodiment of the present invention is represented by the following Formula 1.

[Formula 1]

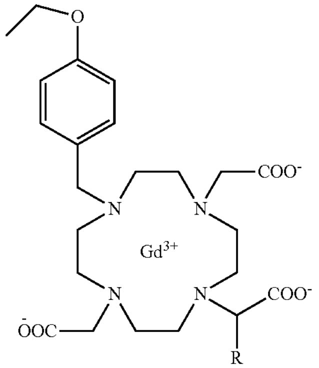

In Formula 1 above, R represents —COO—, —$CH_2COO$— or —$CH_2CH_2COO$—. Preferably, the R may be —$CH_2COO$— or —$CH_2CH_2COO$—. More preferably, the R may be —$CH_2COO$—.

According to an embodiment of the present invention, Formula 1 above may be represented by the following Chemical Formula 1-1.

[Formula 1-1]

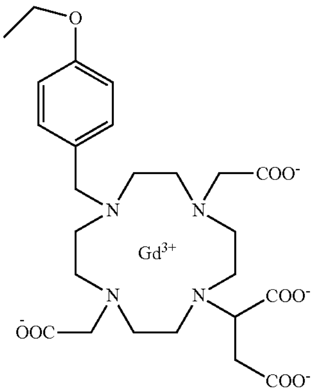

According to an embodiment of the present invention, Formula 1 above may be represented by the following Formula 1-2.

[Formula 1-2]

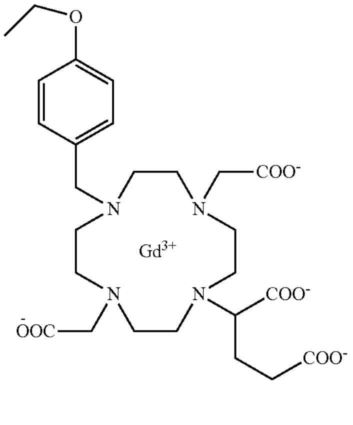

According to an embodiment of the present invention, Formula 1 above may be represented by the following Formula 1-3.

[Formula 1-3]

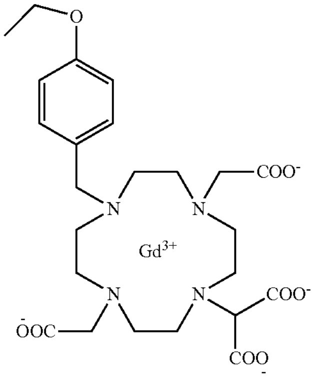

The compound of the present invention represented by Formula 1-1, 1-2, or 1-3 above is synthesized by complexing a ligand, which has a structure such that an ethoxybenzyl group having appropriate lipophilicity is conjugated to an anionic cyclic DOTA backbone, with gadolinium, and it has an appropriate magnetic relaxation rate and can thus be used as an anionic cyclic MRI contrast agent.

According to an embodiment of the present invention, the compound of the present invention can specifically bind to liver tissue. More specifically, the compound of the present invention is introduced into hepatocytes through organic-anion transporting peptide, which is a specific transporter of hepatocytes, etc. to thereby determine whether the hepatocytes can grow normally or abnormally.

The MRI contrast agent according to another embodiment of the present invention contains the compound represented by Formula 1 above.

According to an embodiment of the present invention, the MRI contrast agent has an excellent degree of enhancement of liver contrast compared to other organs in terms of in vivo MRI images, and as described above, the MRI contrast agent can be introduced into the liver through a specific transport protein of hepatocytes and enters the liver and thereby can determine whether the cells grow normally or abnormally.

Therefore, the MRI contrast agent can be used for the diagnosis of liver diseases. More specifically, the MRI contrast agent can be used for the diagnosis of cancer metastasis in the liver, liver cyst, liver cancer, or biliary obstruction.

According to an embodiment of the present invention, the MRI contrast agent is characterized in that it has a magnetic relaxation rate of 5 $mM^{-1}s^{-1}$ to 10 $mM^{-l}s^{-1}$ in the 4.7 T magnetic resonance imaging.

Since the MRI contrast agent of the present invention has superior kinetic stability compared to a clinical liver-specific MRI contrast agent having a linear structure, it improves in vivo stability and minimizes side effects of the MRI contrast agent due to in vivo gadolinium ion leakage; therefore, it can be utilized as a liver-specific MRI contrast agent for clinical use.

In particular, the MRI contrast agent containing the compound represented by Formula 1-1 above has high kinetic stability, and this is because the stability of compound is optimized due to the alkyl chain structure of the compound.

Hereinafter, in order to help better understand the present invention, a compound according to the present invention,

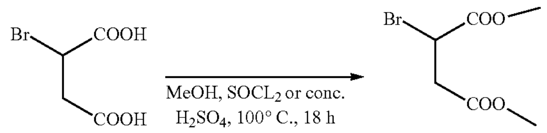

1

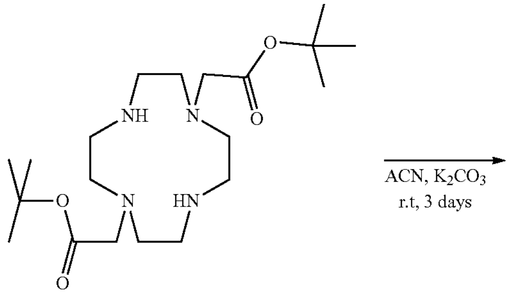

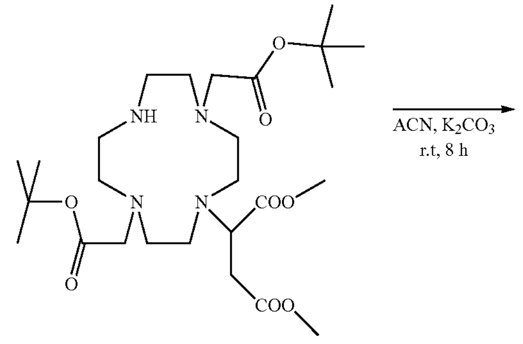

2

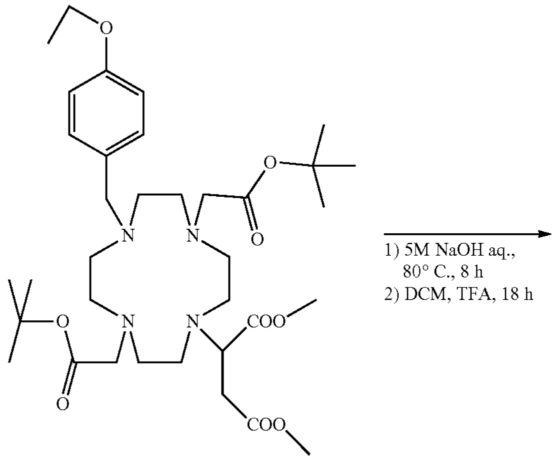

3

-continued

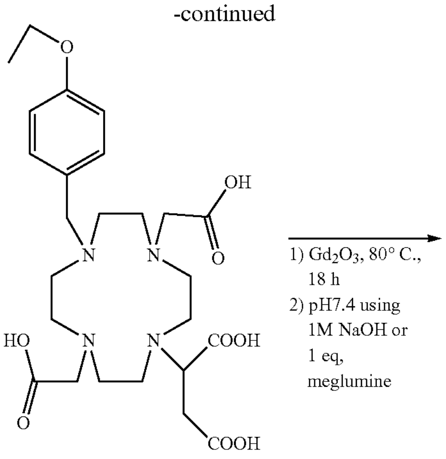

4

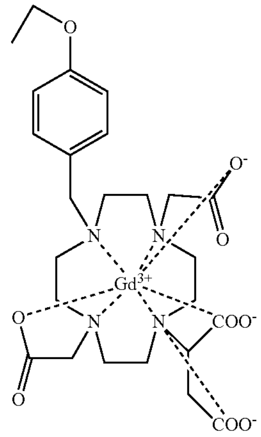

5 a preparation method thereof, and an MRI contrast agent containing the same will be described using representative compounds of the present invention. However, the present invention is not limited by the following examples.

1. Synthesis of Compounds According to Embodiments of the Present Invention

1-1. Example 1 (Synthesis of Gd-suc)

1) Synthesis of dimethyl-2-bromosuccinate (1)

Method 1) Sulfuric acid (1.3 mL, 95% grade) was added to a solution of bromosuccinic acid (5 g, 25.38 mmol) dissolved in methanol (75 mL) at room temperature while stirring. Then, the colorless reaction solution was heated and stirred at 120° C. for 1 hour in a reflux device.

After completion of the reaction, the reactants were cooled at room temperature, and methanol was removed by rotary evaporation, and a 5% $NaHCO_3$ solution was added thereto to neutralize the reactants to pH 6, and then diethyl ether (200 ml) was added thereto to extract the reactants. The extraction process using a 5% $NaHCO_3$ solution and diethyl ether was repeated twice, and then the organic layer containing the product was washed again twice using a saturated NaCl solution. After completion of extraction and washing, the organic layer was dehydrated by adding anhydrous $MgSO_4$ thereto and then subjected to rotary evaporation to obtain a colorless oily product (1) (4.91 g, 21.83 mmol, 86%).

Method 2) Thionyl chloride (3.66 mL, 50.76 mmol) was dissolved in methanol (120 mL) and then slowly added to a solution of bromosuccinic acid (5 g, 25.38 mmol) cooled to 0° C. while stirring. After completion of adding thionyl chloride, the temperature of the reaction mixture was raised to room temperature and reacted by stirring for 24 hours.

After completion of the reaction, methanol was removed by rotary evaporation and neutralized by adding a 5% $NaHCO_3$ solution thereto. Diethyl ether (200 mL) was added to the neutralized reactants to extract the reactants. The extraction process using a 5% $NaHCO_3$ solution and diethyl ether was repeated twice, and then the organic layer containing the product was washed again twice using a saturated NaCl solution. After completion of extraction and washing, the organic layer was dehydrated by adding anhydrous $MgSO_4$ thereto and then subjected to rotary evaporation to obtain a colorless oily product (1). The resulting oil was obtained by silica column (petroleum ether/ethyl acetate) (4.63 g, 20.56 mmol, 81%). $^1$H NMR (500 MHz, $CDCl_3$) δ 4.55 (dd, J=8.8, 6.2 Hz, 1H), 3.78 (s, 3H), 3.68 (s, 3H), 3.25 (dd, J=17.2, 8.8 Hz, 1H), 2.96 (dd, J=17.2, 6.2, 3.3 Hz, 1H). The $^1$H NMR (500 MHz) spectrum of the product (1) is shown in FIG. 1.

2) Synthesis of dimethyl 2-(4,10-bis(2-(tert-butoxy)-2-oxoethyl)-1,4,7,10-tetraazacyclododecan-1-yl)succinate (2)

A solution of dimethyl-2-bromosuccinate (1) (0.5 g, 2.22 mmol) dissolved in ACN (20 ml) was slowly added to a mixed solution (ACN, 100 mL) of di-tert-butyl 2,2'-(1,4,7,10-tetraazacyclododecane-1,7-diyl)diacetate (0.89 g, 2.22 mmol) and $NaHCO_3$ (1.23 g, 8.89 mmol) at room temperature for 2 days (syringe pump: 0.35 mL/hr) while stirring. The completion time of the reaction was confirmed through LC/MS or thin layer chromatography (silica, DCM: MeOH=95:5).

Figure 2:
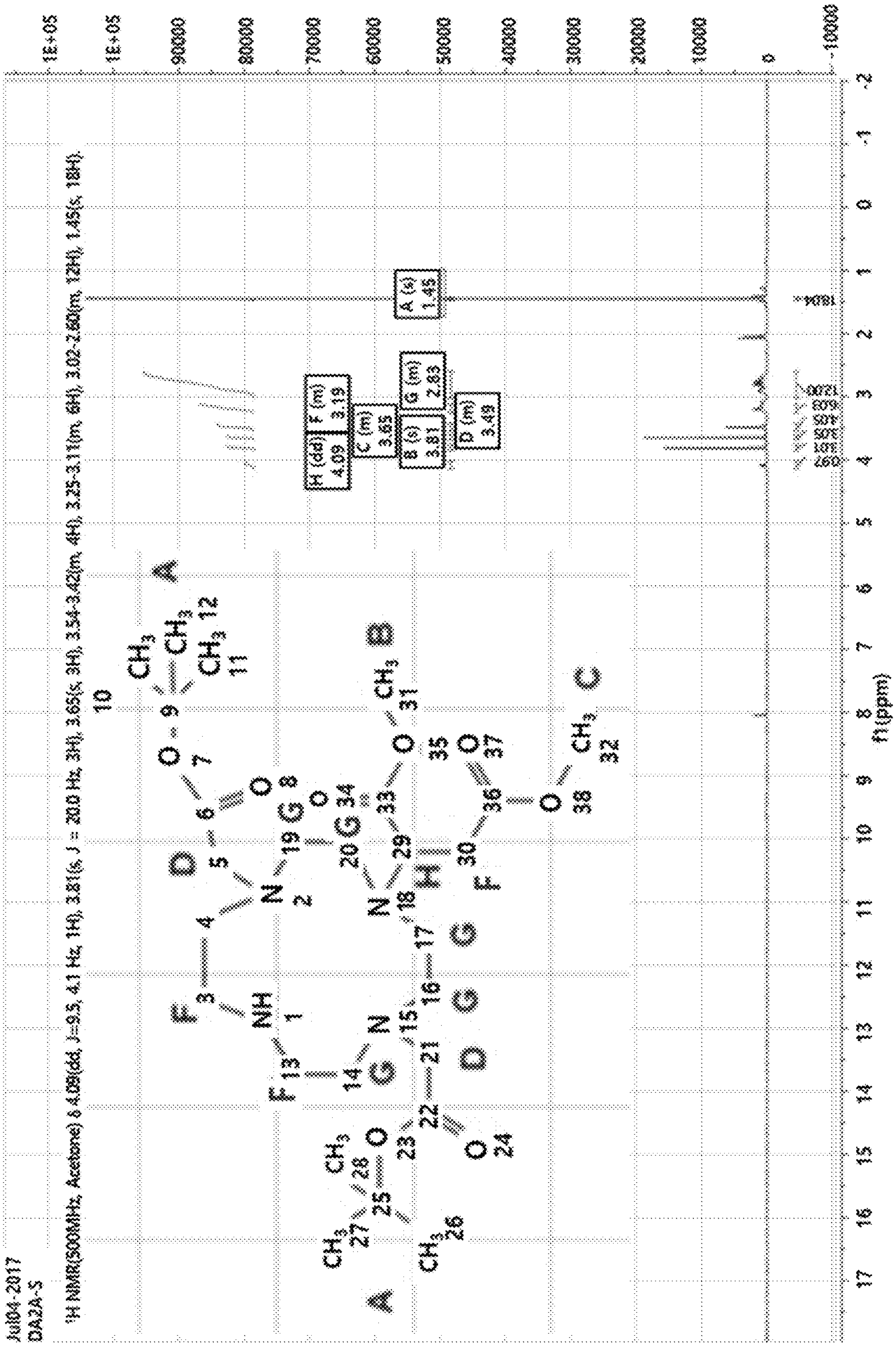
FIG. 2 shows the $^{1}H$ NMR (500 MHz) spectrum of Compound (2) produced during the synthesis of the compound according to the present invention.

After completion of the reaction, the alkali solid was removed by filtration, and the ACN of the reactants was removed by rotary evaporation under reduced pressure. The reactants were recrystallized in n-hexane to obtain a colorless crystal product (2) (0.94 g, 1.73 mmol, 78%). $^1$H NMR (500 MHz, Acetone-d) δ 4.09 (dd, J=9.5, 4.1 Hz, 1H), 3.81 (s, J=20.0 Hz, 3H), 3.65 (s, 3H), 3.54-3.42 (m, 4H), 3.25-3.11 (m, 6H), 3.02-2.60 (m, 12H), 1.45 (s, 18H). The $^1$H NMR (500 MHz) spectrum of the product (2) is shown in FIG. 2.

3) Synthesis of dimethyl 2-(4,10-bis(2-(tert-butoxy)-2-oxoethyl)-7-(4-ethoxybenzyl)-1,4,7,10-tetraazacyclododecan-1-yl)succinate (3)

1-(Chloromethyl)-4-ethoxybenzene (2.69 g, 15.76 mmol) was added to a mixed solution (ACN, 100 mL) of the above product (2) (5.17 g, 9.49 mmol) and $K_2CO_3$ (3.93 g, 28.47 mmol) at room temperature and stirred at room temperature for 18 hours. The completion of the reaction was confirmed through LC/MS or thin layer chromatography (silica, DCM: MeOH=95:5).

After completion of the reaction, the alkali solid was removed by filtration, and the ACN was removed by rotary evaporation under reduced pressure. The reaction mixture from which the solvent was removed was dissolved by adding diethyl ether (300 mL) thereto, and extraction was performed three times by adding a 1 M aqueous HCl solution was added thereto. After removing the by-product of the organic layer and neutralizing the remaining aqueous layer to pH 6 to 7 by adding a 3 M NaOH solution thereto, the product was precipitated as a white solid, and DCM (300 mL) was added thereto to extract the product as an organic layer. The organic layer from which the product was extracted was dehydrated with anhydrous $MgSO_4$ and then subjected to rotary evaporation to obtain a pale yellow solid, which was further purified by a silica column (chloroform/MeOH) to obtain a white solid product (3) (5.35 g, 7.88 mmol, 83%).

4) Synthesis of 2-(4,10-bis(carboxymethyl)-7-(4-ethoxybenzyl)-1,4,7,10-tetraazacyclododecan-1-yl) succinic acid (4)

The product (3) (4.68 g, 6.89 mmol) was dissolved in THF (175 mL) and a 0.3 M aqueous LiOH solution (175 mL) and the mixture was stirred at room temperature for 18 hours. The completion time of the reaction was confirmed by LC/MS, and after completion of the reaction, THF was removed and the volume of water was reduced to 10 mL by rotary evaporation under reduced pressure. The reaction mixture was acidified by passing through washed amberlite IR 120 ($H^+$ form), and water was removed from the reactants. The reactants were again dissolved in DCM (150 mL) and trifluoroacetic acid (150 mL) and reacted for 18 hours.

Figure 3:
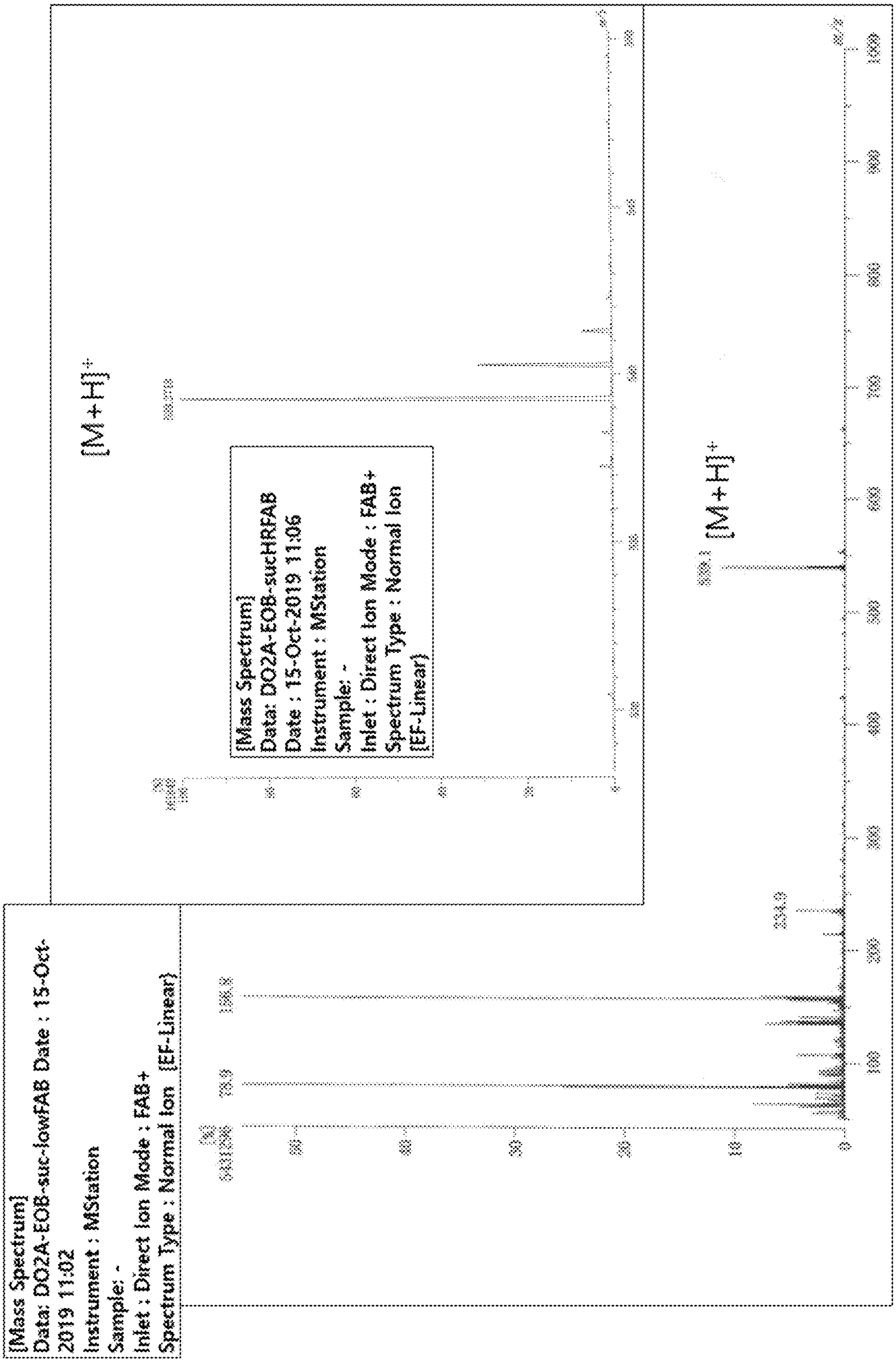
FIG. 3 shows the results of HR-FABMS (positive mode) analysis of Compound (4) produced during the synthesis of the compound according to the present invention.

After completion of the reaction, all the solvents in the reaction mixture from which the protecting group was removed was removed and dissolved in methanol to purify and obtained a precipitate under diethyl ether conditions. The precipitate was dissolved in tertiary distilled water containing 0.1% TFA and purified by flash chromatography (Biotage, sfar C18, 30 g) or semi-prep HPLC (YMC, Hydrosphere C18) to finally obtain a white solid product (4). (3.38 g, 6.27 mmol, 91%), HR-FABMS: Calc. 539.2717, found. 539.2718 $[M+H]^+$. The results of HR-FABMS (positive mode) analysis of the product (4) are shown in FIG. 3.

Synthesis of Gadolinium Complex (Gd-Suc) (5)

sodium salt) $Gd_2O_3$ (1.07 g, 2.95 mmol) was added to a solution, in which the product (4) (0.317 g, 5.89 mmol) was dissolved in tertiary distilled water (40 mL), and the mixture was stirred at 90° C. for 18 hours. The completion time of the reaction was confirmed through LC/MS or thin layer chromatography (C18, water:ACN=7:3).

After completion of the reaction, the resultant was adjusted to pH 7 by adding a 1 M aqueous NaOH solution, and purified by flash chromatography (Biotage, sfar C18, 30 g) or semi-prep HPLC (YMC, Hydrosphere C18) to finally obtain a gadolinium complex (5) as a white solid.

meglumine salt) $Gd_2O_3$ (1.07 g, 2.95 mmol) was added to a solution, where the product (4) (0.317 g, 5.89 mmol) was dissolved in tertiary distilled water (40 mL), and the mixture was stirred at 90° C. for 18 hours. The completion time of the reaction was confirmed through LC/MS or thin layer chromatography (C18, water:ACN=7:3).

Figure 4:
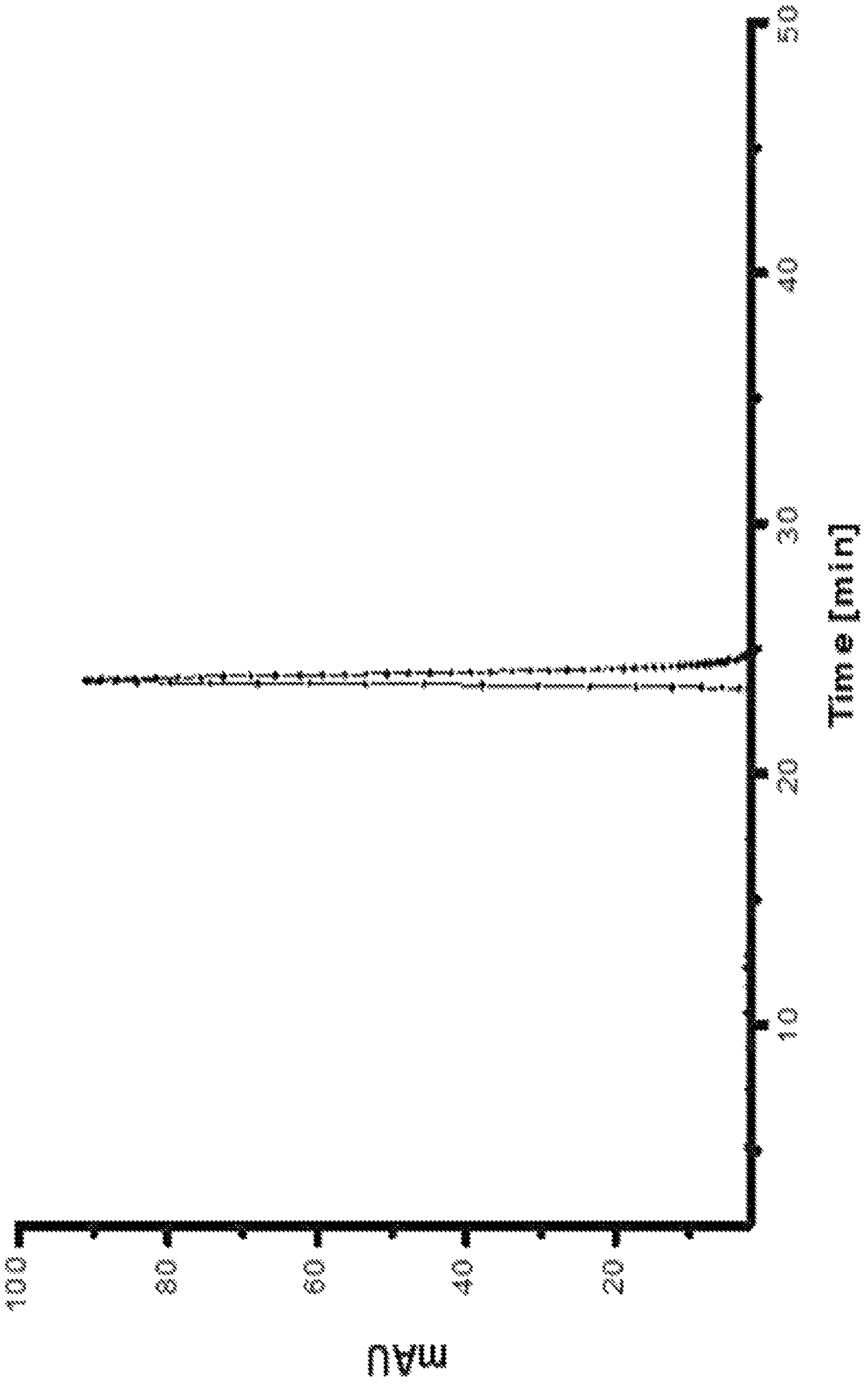
FIG. 4 shows the results of HPLC analysis of the (Gd-suc) compound according to Example 1 of the present invention.
Figure 5:
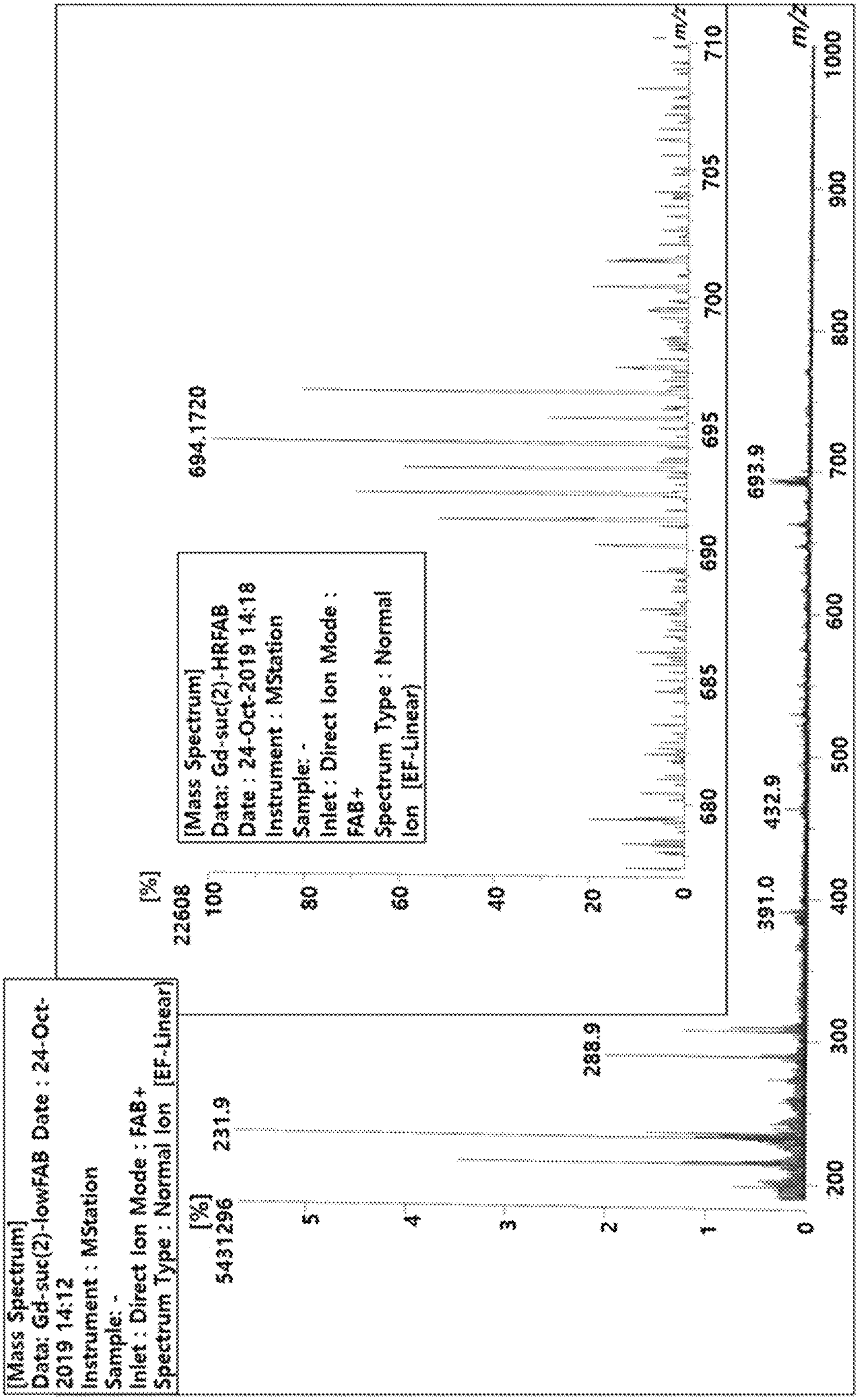
FIG. 5 shows the results of HR-FABMS (positive mode) analysis of the (Gd-suc) compound according to Example 1 of the present invention.
Figure 6:
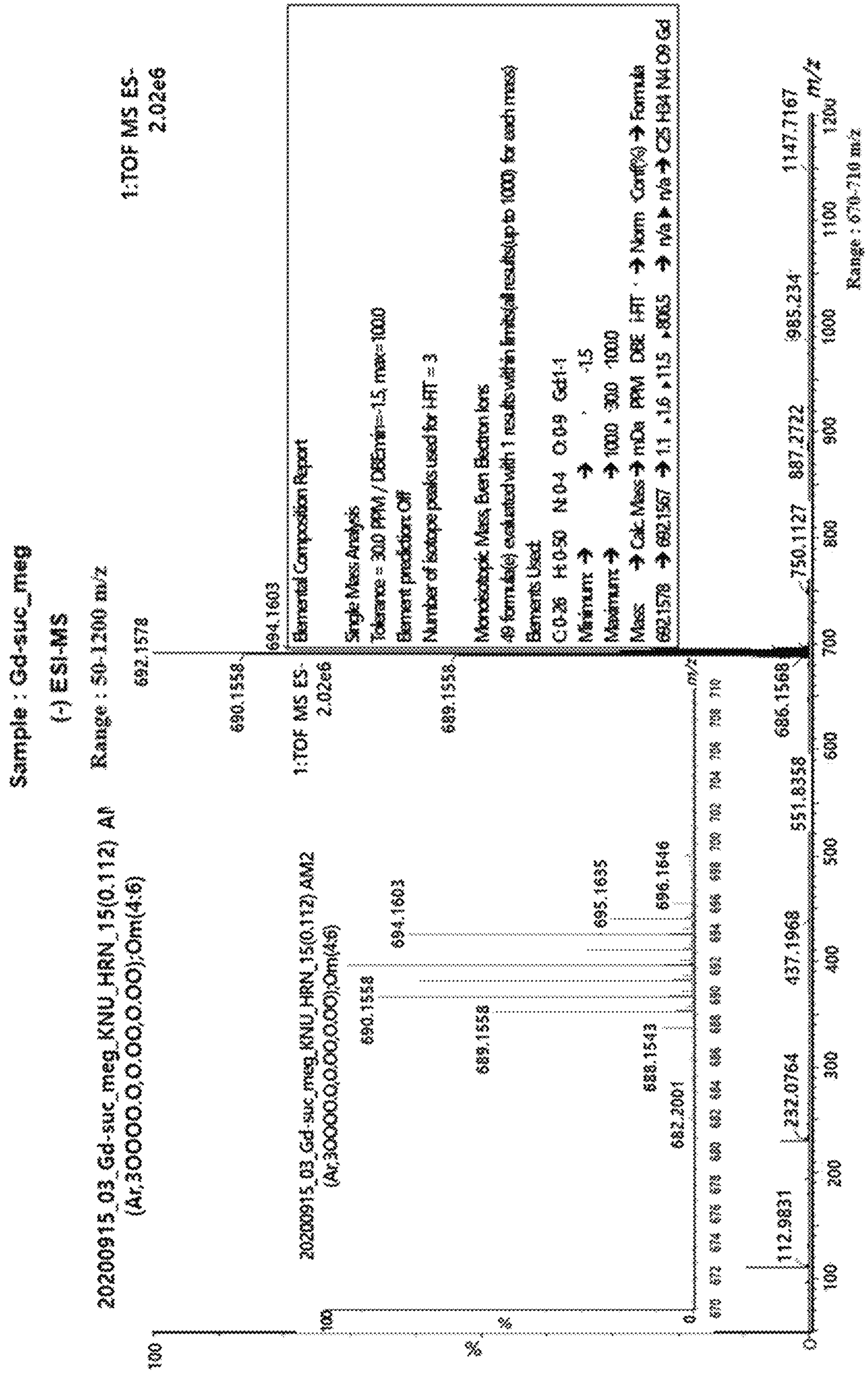
FIG. 6 shows the results of HR-ESIMS (negative mode) analysis of the (Gd-suc) compound according to Example 1 of the present invention.

After completion of the reaction, the product was purified by flash chromatography (Biotage, sfar C18, 30 g) or semi-prep HPLC (YMC, Hydrosphere C18), and meglumine (5.89 mmol) was added to the purified product for chlorination and lyophilized to give a white color. A solid gadolinium complex (5) (hereinafter referred to as Gd-suc) was obtained (3.79 g, 5.48 mmol, 93%). HR-FABMS: Calc. 694.1723, found. 694.1720 $[M+2H]^+$, HR-ESIMS: Calc. 692.1537, found. 692.1578, $[M]^-$. The results of HPLC analysis of the Gd-suc (5), HR-FABMS (positive mode), and HR-ESIMS (negative mode) analysis are shown in FIGS. 4 to 6, respectively.

1-2. Example 2 (Synthesis of Gd-glu)

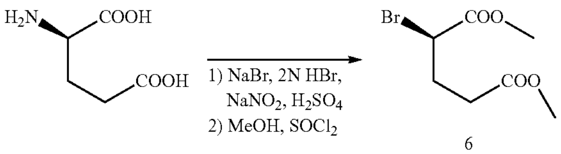

6

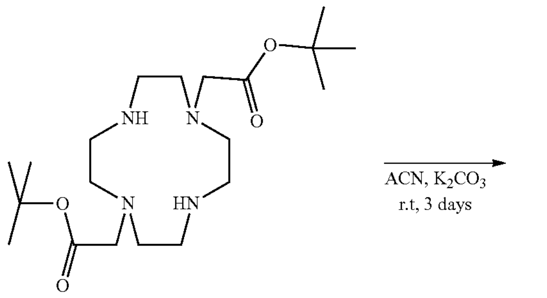

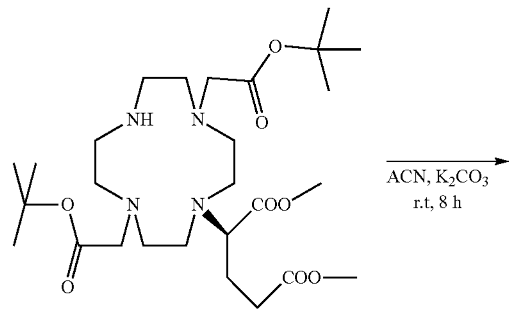

7

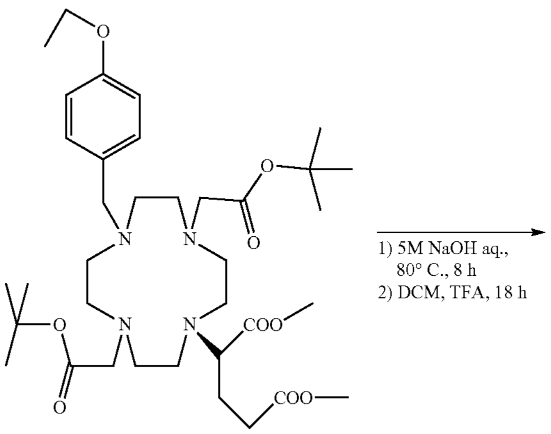

8

-continued

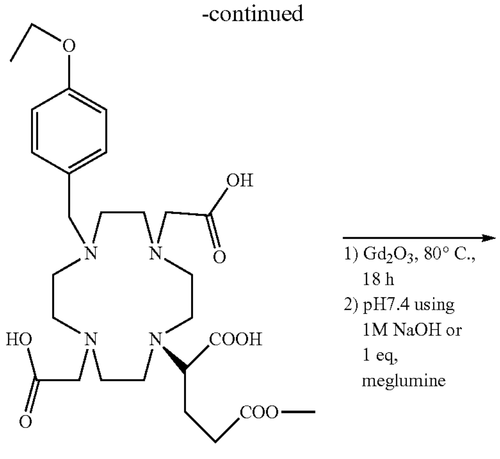

9

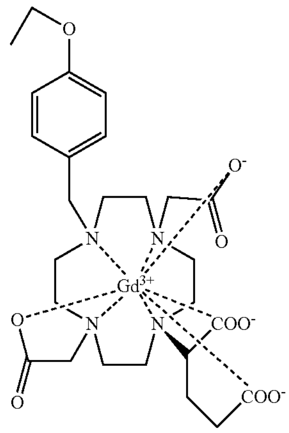

10

1) Synthesis of dimethyl (R)-2-bromonpentanedioate (6)

Sodium nitrite (15.6 g, mmol) was slowly added for 30 minutes to a reaction mixture at 0° C., in which L-glutaric acid (15 g, mmol) and sodium bromide (26.22 g, mmol) were dissolved in a 2 N HBr solution (125 mL). After completion of the addition, the mixture was stirred at room temperature for 5 minutes, sulfuric acid (95%, 5 mL) was added to the reaction mixture stirred at room temperature, and the resultant was stirred at room temperature for 1.5 hours.

Diethyl ether (200 mL) was added to the reaction mixture, and the process of extracting a product through the organic layer was repeated three times. The extracted organic layer was dehydrated using anhydrous $MgSO_4$ and then subjected to rotary evaporation under reduced pressure to obtain a yellow oil. The yellow oil was dissolved in MeOH (65 mL), and then $SOCl_2$ (4 mL) was added thereto to react at room temperature for 2 days.

After completion of the reaction, the excess $SOCl_2$ was neutralized with a 5% NaHCO solution and then extracted with DCM (150 mL). The extracted organic layer was dehydrated over anhydrous $MgSO_4$ and then subjected to rotary evaporation under reduced pressure to obtain a light yellow oil. The light yellow oil was purified using a silica column (petroleum ether/ethyl acetate) to obtain a colorless oil product (6) (5.29 g, 0.022 mmol, 21.57%). $^1H$ NMR (500

Figure 7:
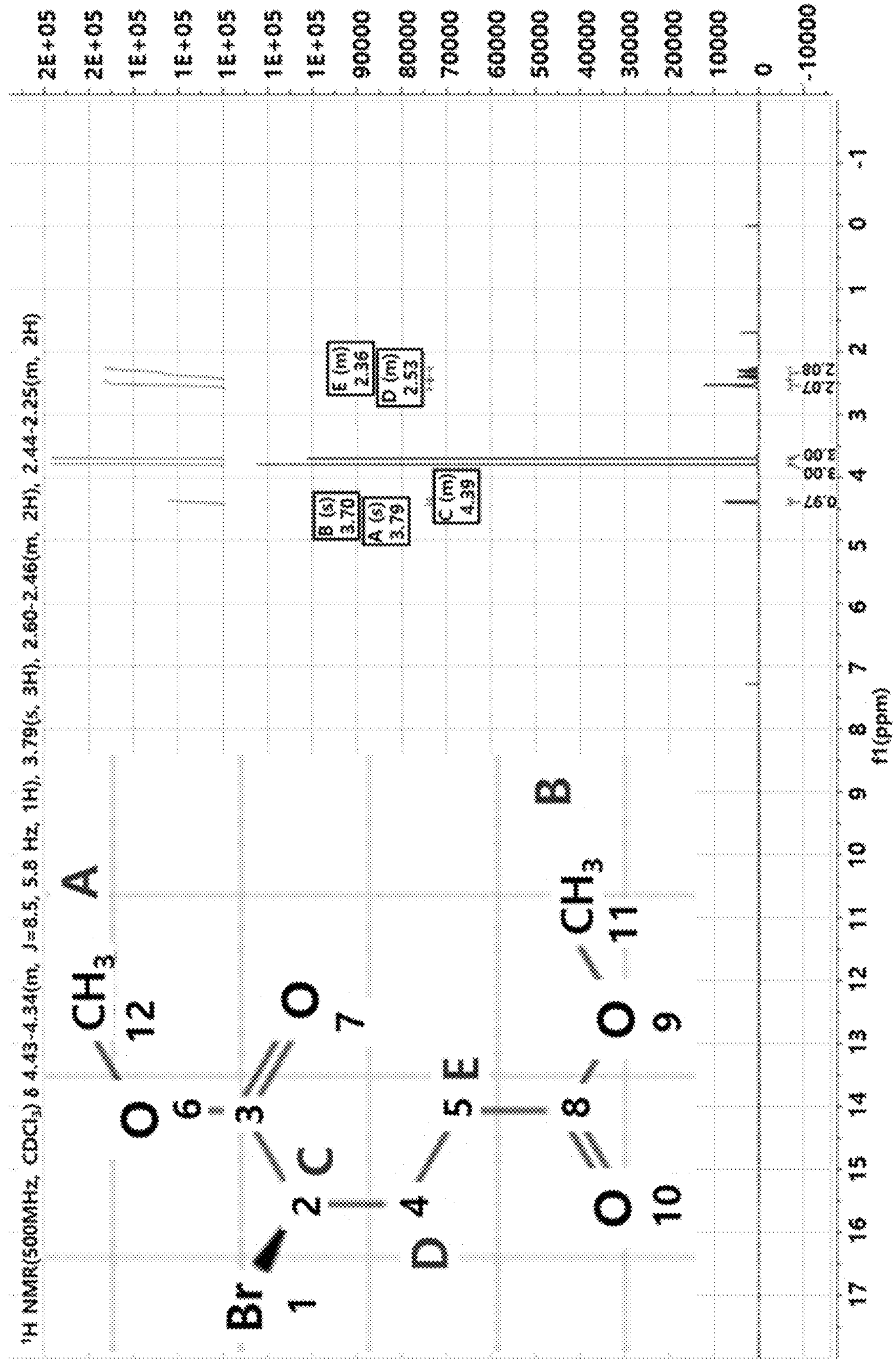
FIG. 7 shows the $^{1}H$ NMR (500 MHz) spectrum of Compound (6) produced during the synthesis of the compound according to the present invention.

MHz, $CDCl_3$) δ 4.43-4.34 (m, J=8.5, 5.8 Hz, 1H), 3.79 (s, 3H), 3.70 (s, 3H), 2.60-2.46 (m, 2H), 2.44-2.25 (m, 2H). The $^1H$ NMR (500 MHz) spectrum of the product (6) is shown in FIG. 7.

2) Synthesis of dimethyl (R)-2-(4,10-bis(2-(tert-butoxy)-2-oxoethyl)-1,4,7,10-tetraazacyclododecan-1-yl)pentanedioate (7)

A solution of dimethyl (R)-2-bromopentanedioate (6) (5.1 g, 21.33 mmol) dissolved in ACN (100 mL) was slowly added to a mixed solution ACN (100 mL) of di-tert-butyl 2,2'-(1,4,7,10-tetraazacyclododecane-1,7-diyl)diacetate (8.55 g, 21.33 mmol) and $K_2CO_3$ (2.95 g, 21.33 mmol) at room temperature for 2 days (syringe pump: 5 mL/hr) while stirring (syringe pump: 5 mL/hr). The completion time of the reaction was confirmed through LC/MS or thin layer chromatography (silica, DCM:MeOH=95:5).

Figure 8:
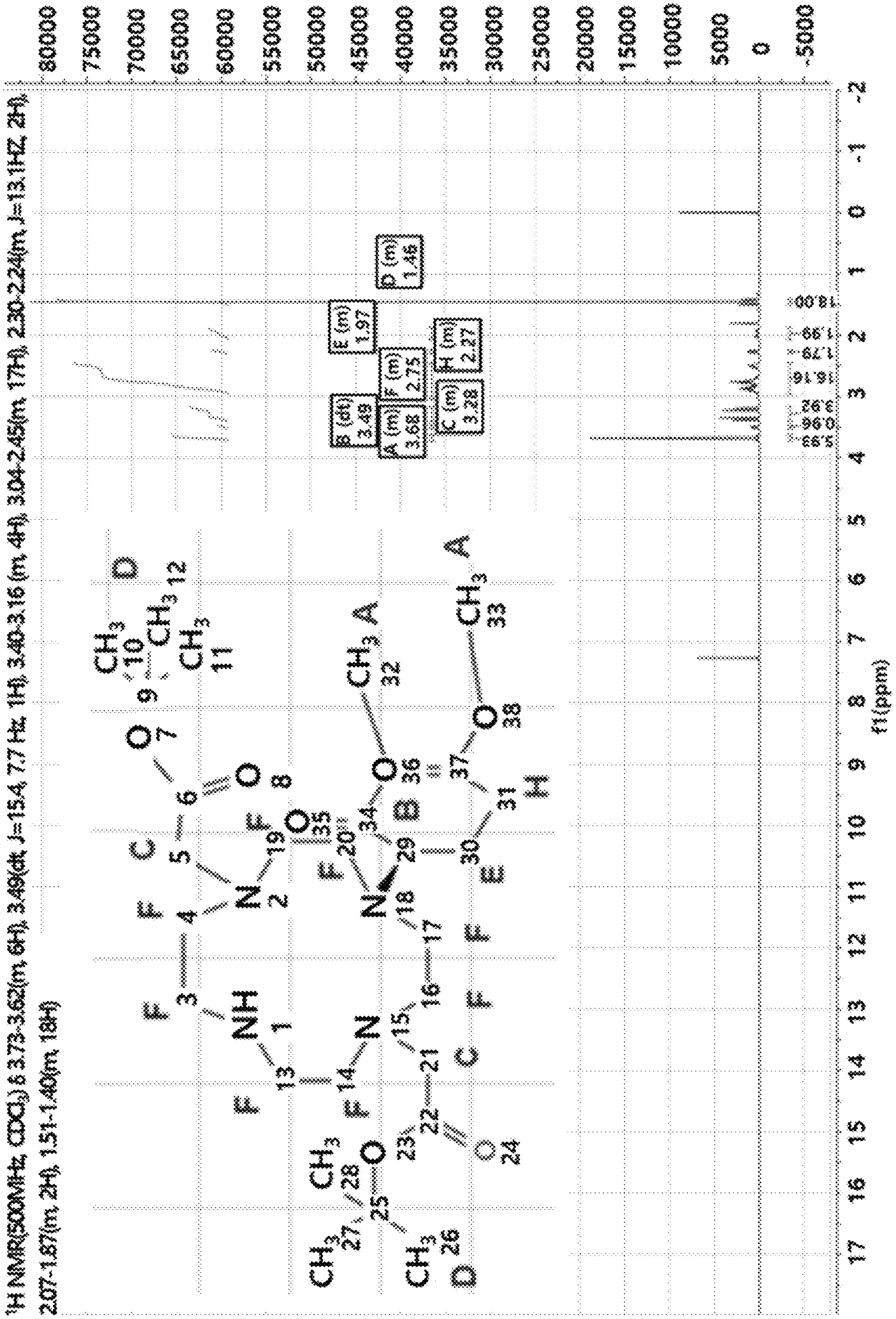
FIG. 8 shows the $^{1}H$ NMR (500 MHz) spectrum of Compound (7) produced during the synthesis of the compound according to the present invention.

After completion of the reaction, the alkali solid was removed by filtration, and ACN of the reactants was removed by rotary evaporation under reduced pressure to obtain a light yellow oil. The light yellow oil was subjected to silica column ($CHCl_3$/MeOH) to obtain a colorless oil, which was precipitated in diethyl ether to obtain a white solid product (7) (9.17 g, 16.44 mmol, 56%). $^1H$ NMR (500 MHz, $CDCl_3$) δ 3.73-3.62 (m, 6H), 3.49 (dt, J=15.4, 7.7 Hz, 1H), 3.40-3.16 (m, 4H), 3.04-2.45 (m, 17H), 2.30-2.24 (m, J=13.1 Hz, 2H), 2.07-1.87 (m, 2H), 1.51-1.40 (m, 18H). The $^1H$ NMR (500 MHz) spectrum of the product (7) is shown in FIG. 8.

3) Synthesis of dimethyl (S)-2-(4,10-bis(2-(tert-butoxy)-2-oxoethyl)-7-(4-ethoxybenzyl)-1,4,7,10-tetraazacyclododecan-1-yl) pentanedioate (8)

1-(Chloromethyl)-4-ethoxybenzene (0.93 g, 5.34 mmol) was added to the mixed solution (ACN, 60 mL) of the product (7) (1.99 g, 3.56 mmol) and $K_2CO_3$ (1.48 g, 10.69 mmol) at room temperature and stirred at room temperature for 18 hours. The completion time of the reaction was confirmed through LC/MS or thin layer chromatography (silica, DCM:MeOH=95:5).

After completion of the reaction, the alkali solid was removed by filtration, and ACN was removed by rotary evaporation under reduced pressure. To the reaction mixture from which the solvent is removed, was dissolved by adding diethyl ether (100 mL) thereto, and extraction was performed three times by adding a 1 M HCl aqueous solution thereto. After removing the by-product of the organic layer and neutralizing the pH of the remaining aqueous layer to pH 6 to 7 by adding a 3 M NaOH solution, the product was precipitated as a white solid, and DCM (100 mL) was added thereto to extract the product as an organic layer. The organic layer from which the product was extracted was dehydrated with anhydrous $MgSO_4$, and was subjected to rotary evaporation to obtain a pale yellow solid, which was further purified by a silica column (chloroform/MeOH) to obtain a white solid product (8) (0.70 g, 1.01 mmol, 28.37%).

4) Synthesis of (S)-2-(4,10-bis(carboxymethyl)-7-(4-ethoxybenzyl)-1,4,7,10-tetraazacyclododecan-1-yl)pentanedioic acid (9)

The product (8) (0.7 g, 1.01 mmol) was dissolved in a 5 M aqueous NaOH solution (4.4 mL) and MeOH (4.4 mL) and the resultant was stirred at room temperature for 18 hours. The completion time of the reaction was confirmed by LC/MS, and after completion of the reaction, the resultant was subjected to rotary evaporation under reduced pressure to remove MeCOH and the water volume was reduced to 2 mL.

The reaction mixture was acidified by passing it through washed amberlite IR 120 ($H^+$ form), and the water in the reaction product was removed. The reactants were once again dissolved in DCM (50 mL) and trifluoroacetic acid (50 mL) and reacted for 18 hours.

Figure 9:
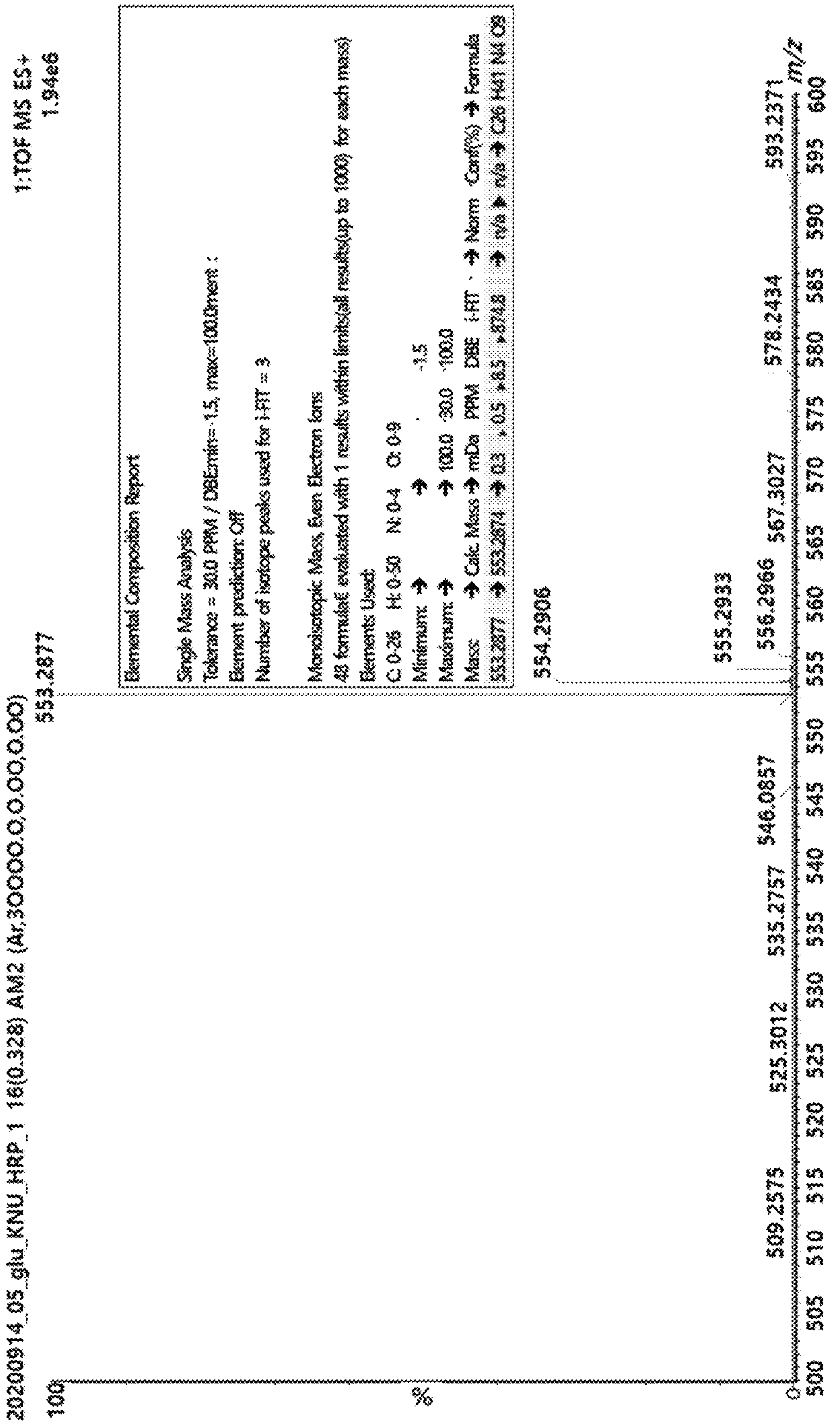
FIG. 9 shows the results of HR-ESIMS (negative mode) analysis of Compound (9) produced during the synthesis of the compound according to the present invention.

After completion of the reaction, all the solvents in the reaction mixture from which the protecting group was removed were removed and then dissolved in methanol to purify and obtain a precipitate under diethyl ether conditions. The precipitate was dissolved in tertiary distilled water containing 0.1% TFA and purified by flash chromatography (Biotage, sfar C18, 30 g) or semi-prep HPLC (YMC, Hydrosphere C18) to finally obtain a white solid product (9) (0.24 g, 0.43 mmol, 43%). HR-ESIMS: Calc. 553.2874, found. 553.2877, $[M+H]^+$. The results of HR-ESIMS (positive mode) analysis of the product (9) are shown in FIG. 9.

5) Synthesis of Gadolinium Complex (Gd-Glu) (10)

sodium salt) $Gd_2O_3$ (0.295 g, 0.453 mmol) was added to a solution where the product (9) (0.5 g, 0.905 mmol) was dissolved in tertiary distilled water (15 mL), and the mixture was stirred at 90° C. for 18 hours. The completion time of the reaction was confirmed through LC/MS or thin layer chromatography (C18, water:CAN=7:3).

After completion of the reaction, the resultant was adjusted to a pH 7 by adding a 1 M aqueous NaOH solution and purified by flash chromatography (Biotage, sfar C18, 30 g) or semi-prep HPLC (YMC, Hydrosphere C18) to finally obtain a gadolinium complex (10) as a white solid.

meglumine salt) $Gd_2O_3$ (0.295 g, 0.453 mmol) was added to a solution, where the product (9) (0.5 g, 0.905 mmol) was dissolved in tertiary distilled water (15 mL), and the mixture was stirred at 90° C. for 18 hours. The completion time of the reaction was confirmed through LC/MS or thin layer chromatography (C18, water:ACN=7:3).

After completion of the reaction, the resultant was purified by flash chromatography (Biotage, sfar C18, 30 g) or semi-prep HPLC (YMC, Hydrosphere C18). The purified product was chlorinated by adding meglumine (0.905 mmol) and lyophilized to obtain gadolinium complex (10) as a white solid (hereinafter referred to as Gd-glu) (0.44 g, 0.62 mmol, 69%). HR-ESIMS: Calc. 706.1723, found. 706.1734, $[M]^-$. The results of HR-ESIMS (positive mode) analysis of the Gd-glu (10) are shown in FIG. 10.

2. Effect of MRI Contrast

In order to examine the MRI contrast effects of the compounds (Gd-suc, Gd-glu) and commercially available MRI contrast agents according to Examples of the present invention, the magnetic relaxation rates and lipophilicity were analyzed, and the results are shown in Table 1 below.

TABLE 1

| | $r_1$ | $r_2$ | $r_2/r_1$ | Log P |
|---|---|---|---|---|
| Gd-suc | 5.96 ± 0.014 | 5.59 ± 0.74 | 0.94 | −2.50 ± 004 |
| Gd-glu | 8.41 ± 0.084 | 9.92 ± 0.081 | 1.18 | — |
| Primovist | 6.51 ± 0.040 | 7.31 ± 0.42 | 1.12 | −2.91 ± 058 |
| Multihance | 5.09 ± 0.015 | 6.79 ± 0.38 | 1.33 | −2.90 ± 038 |

TABLE 1-continued

| | $r_1$ | $r_2$ | $r_2/r_1$ | Log P |
|---|---|---|---|---|
| Dotarem | 4.19 ± 0.014 | 4.75 ± 0.016 | 1.34 | — |
| Gadovist | 4.12 ± 0.028 | 4.60 ± 0.025 | 1.12 | — |
| Prohance | 3.58 ± 0.017 | 4.58 ± 0.071 | 1.28 | — |
| Omniscan | 3.58 ± 0.014 | 4.46 ± 0.024 | 1.25 | — |
| Magnevist | 3.57 ± 0.007 | 4.95 ± 0.18 | 1.39 | — |

The magnetic relaxation rate ($mM^{-1}s^{-1}$) is a parameter indicating contrast efficiency per unit concentration, and in the case of a $T_1$ contrast agent, the $r_2/r_1$ ratio is known to have a value of 0.5 to 1.5.

Referring to Table 1, in the case of Gd-suc, which is a compound of the present invention, it can be seen that Gd-suc has higher $r_2$, $r_1$ values compared to clinical MRI contrast agents being used as extracellular liquid preparations, and has a magnetic relaxation rate and lipophilicity similar to the clinical MRI contrast agent (Primovist, Multihance) which is used as a liver-specific preparation.

3. Kinetic Stability Evaluation

MRI contrast agents using a gadolinium complexes may have structural instability due to interactions with ions in the body depending on the structure of the ligand. Therefore, in order to evaluate the kinetic stability of the compounds (Gd-suc, Gd-glu) according to embodiments of the present invention and commercially available MRI contrast agents, the changes in the magnetic relaxation rates over time were measured, and the results are shown in FIG. 11.

Specifically, zinc chloride (1 eq. of $ZnCl_2$) was added to each of the solutions (room temperature, 2.5 mM, PBS) in which Gd-suc, Gd-glu, and commercially available MRI contrast agents were dissolved, respectively, and then a metal exchange reaction between gadolinium and zinc ions was induced in the pH environment of body (pH 7.4) and confirmed by measuring magnetic relaxation rates thereof (3T MRI, GE Healthcare, Architect).

Figure 11:
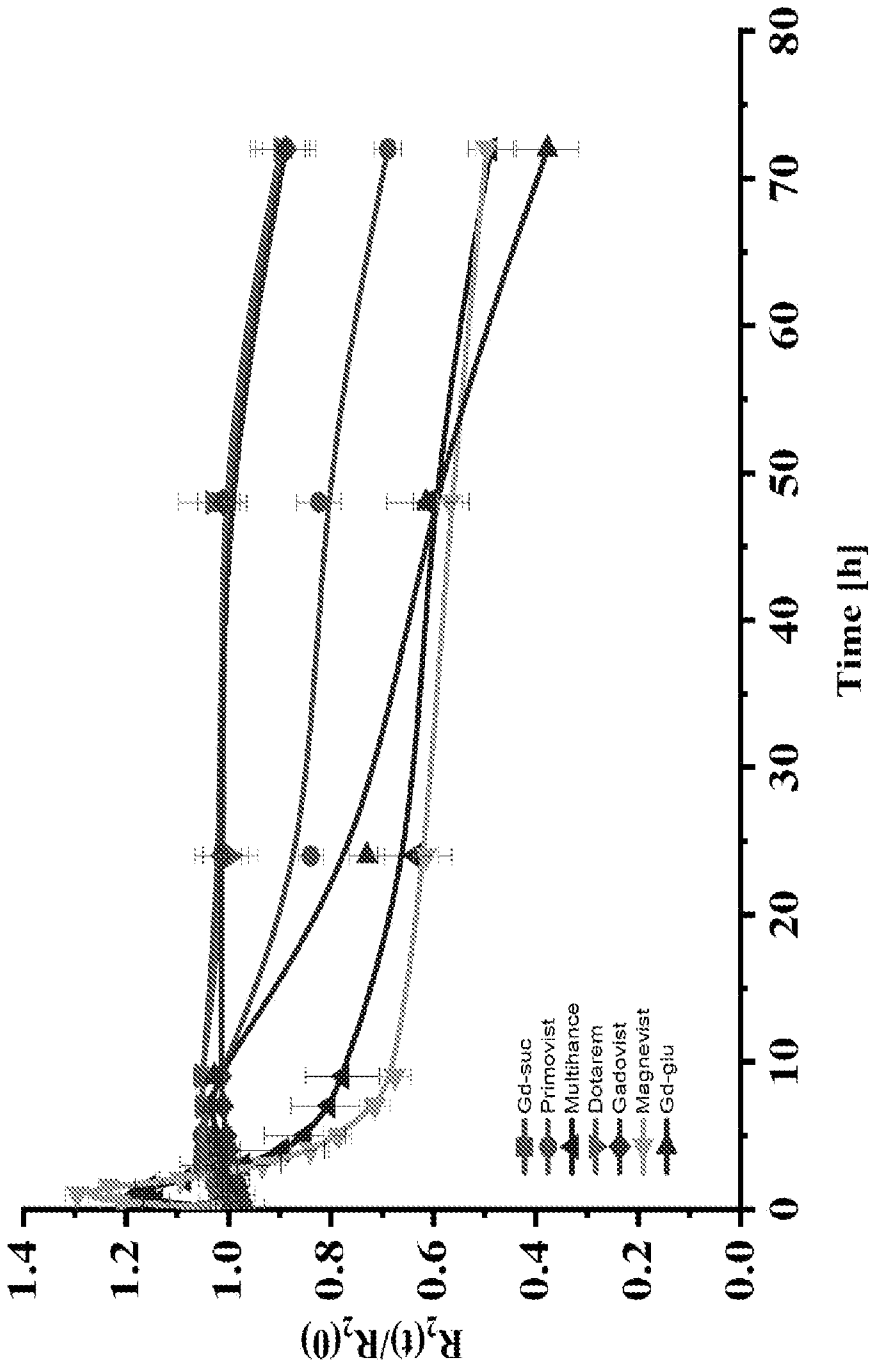
FIG. 11 shows the results of kinetic stability evaluation of the compounds according to an embodiment of the present invention and commercially available contrast agents thereof.

As can be seen in FIG. 11, the compound of the present invention, Gd-suc, showed significantly higher kinetic stability compared to commercially available liver-specific contrast agents Primovist and Multihance, but showed kinetic stability similar to Dotarem, which is Gd-DOTA.

4. In Vivo MRI Contrast Effect

The liver-specific $T_1$ contrast effect of the compounds (Gd-suc, Gd-glu) according to embodiments of the present invention and Primovist, a commercially available liver contrast agent, was evaluated in small animals (Balb/C mice, male, 5 w, 25 g, 0.1 mmol/kg) and confirmed through abdominal $T_1$ weighted images (Bruker, 4.7 T), and the results are shown in FIGS. 12 to 15.

Figure 12:
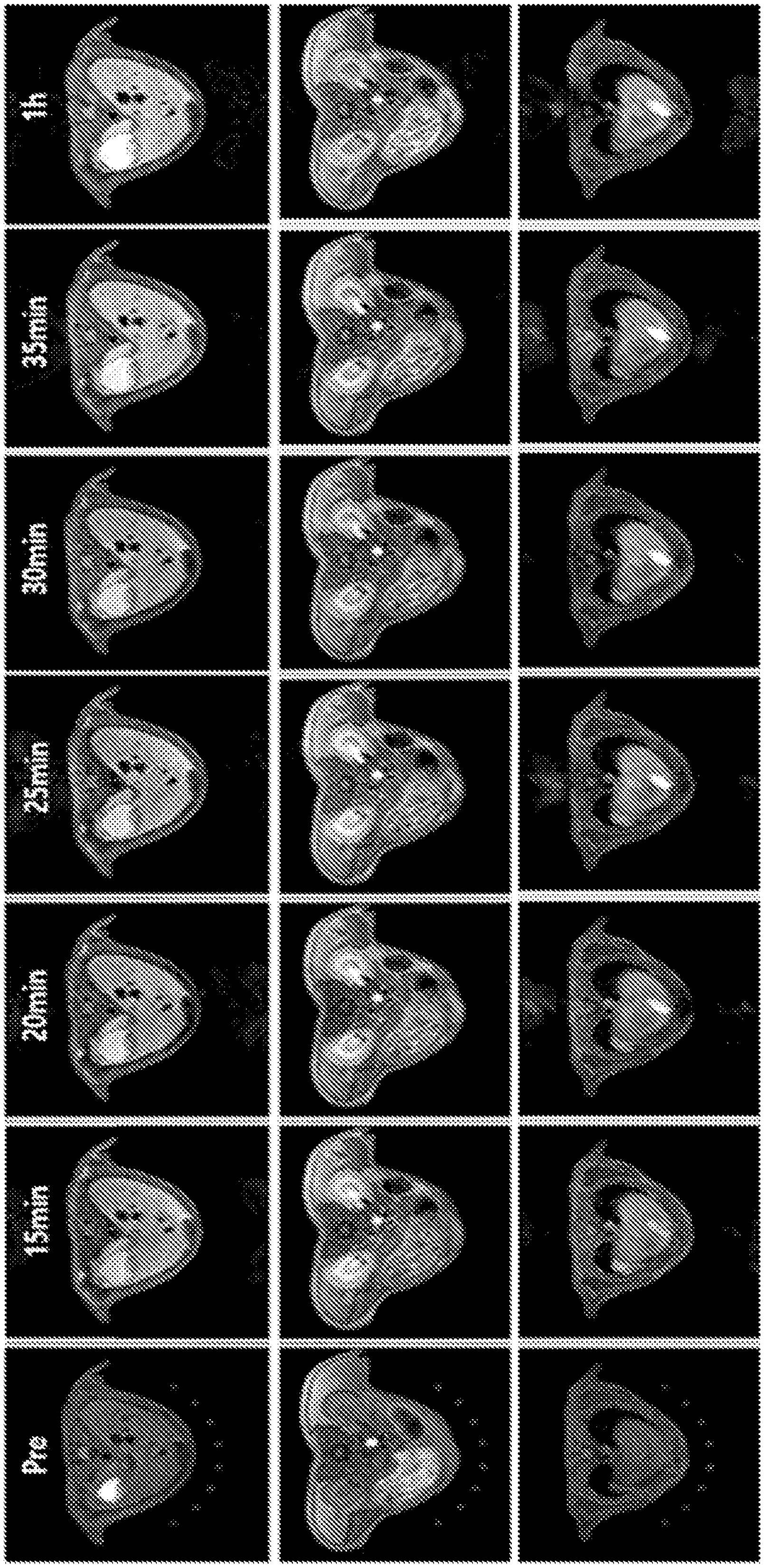
FIG. 12 shows images illustrating the contrast enhancement phenomenon between in vivo $T_1$ MRI according to time of the (Gd-suc) compound according to Example 1 of the present invention.
Figure 13:
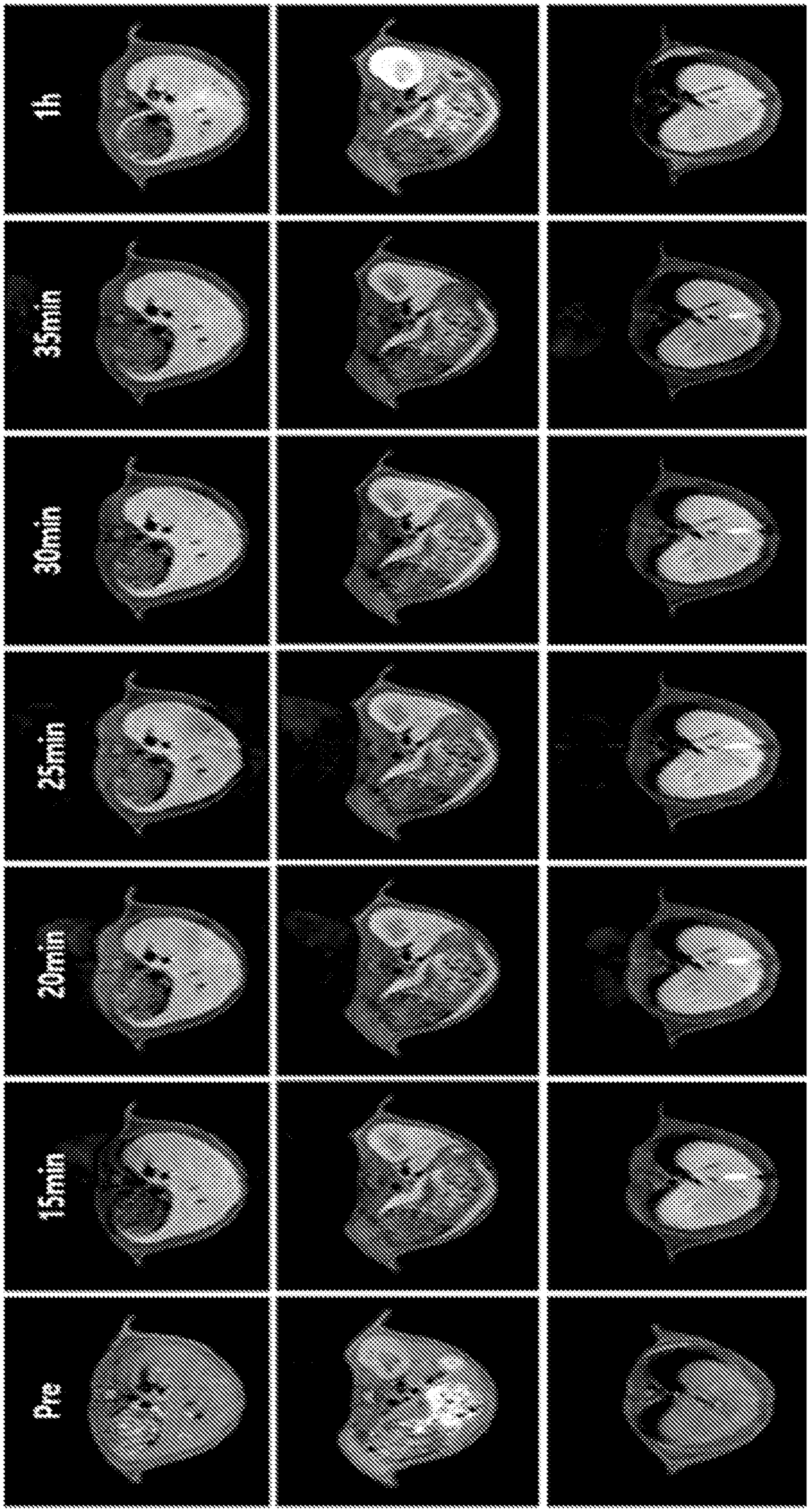
FIG. 13 shows images illustrating the contrast enhancement phenomenon between in vivo $T_1$ MRI according to time of Primovist, which is a commercially available contrast agent.

Referring to FIG. 12, the compound of the present invention, Gd-suc, showed rapid liver-biliary contrast enhancement and release within 15 minutes after caudal intravenous administration to mice. This is a characteristic of a liver-specific contrast agent and can be confirmed as a contrast enhancement phenomenon in the gall bladder.

Additionally, the enhancement level of liver-specific contrast of Gd-suc was shown to be similar to that of Primovist (see FIG. 13), which is a commercially available liver-specific MRI contrast agent.

Figure 14:
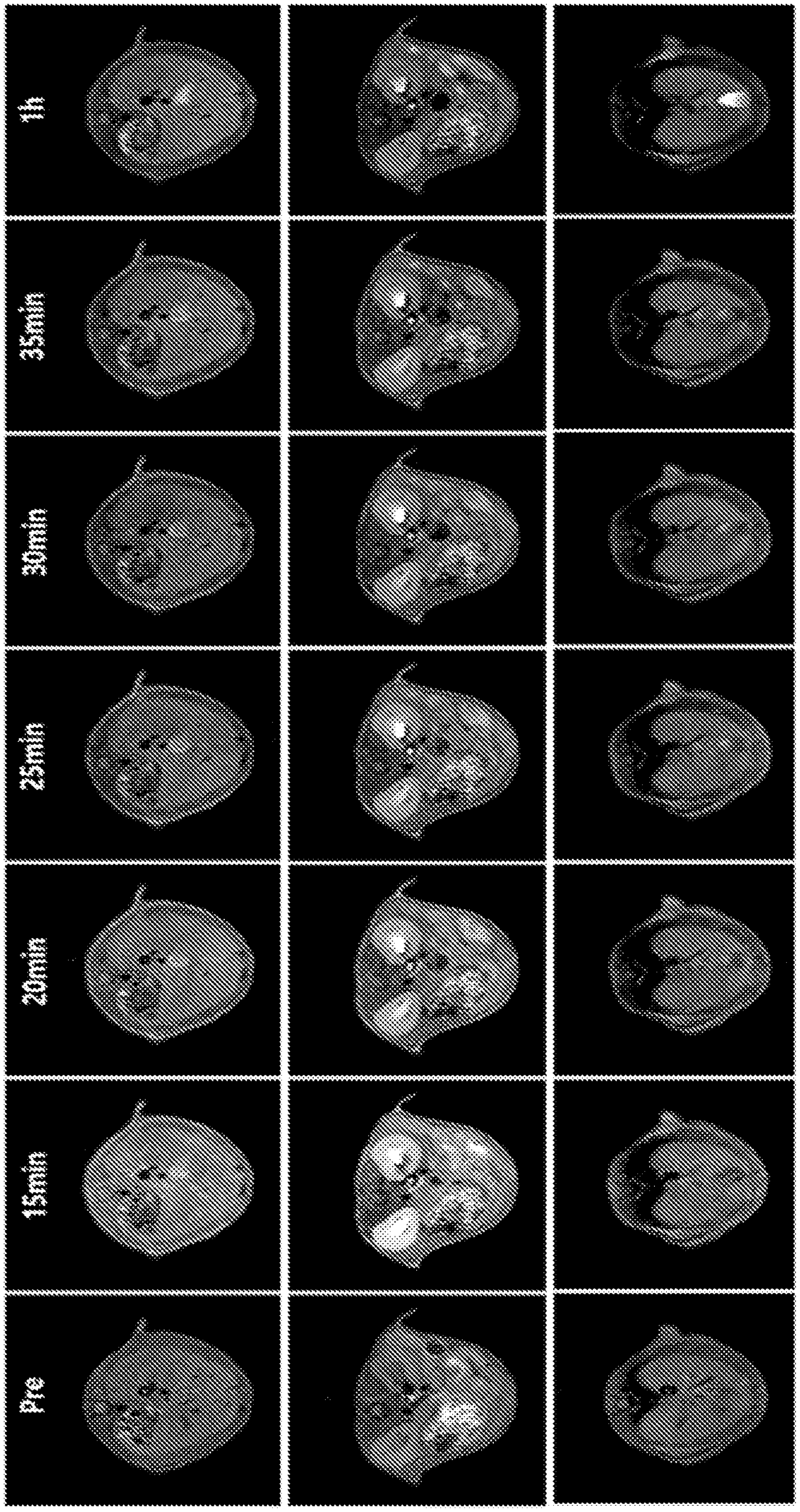
FIG. 14 shows images illustrating the contrast enhancement phenomenon between in vivo $T_1$ MRI according to time of the (Gd-suc) compound according to Example 2 of the present invention.

Meanwhile, referring to FIG. 14, it can be seen that Gd-glu, a compound of the present invention, also exhibited a contrast enhancing effect in the gall bladder, and thus can be used as a liver disease-specific MRI contrast agent.

Figure 15:
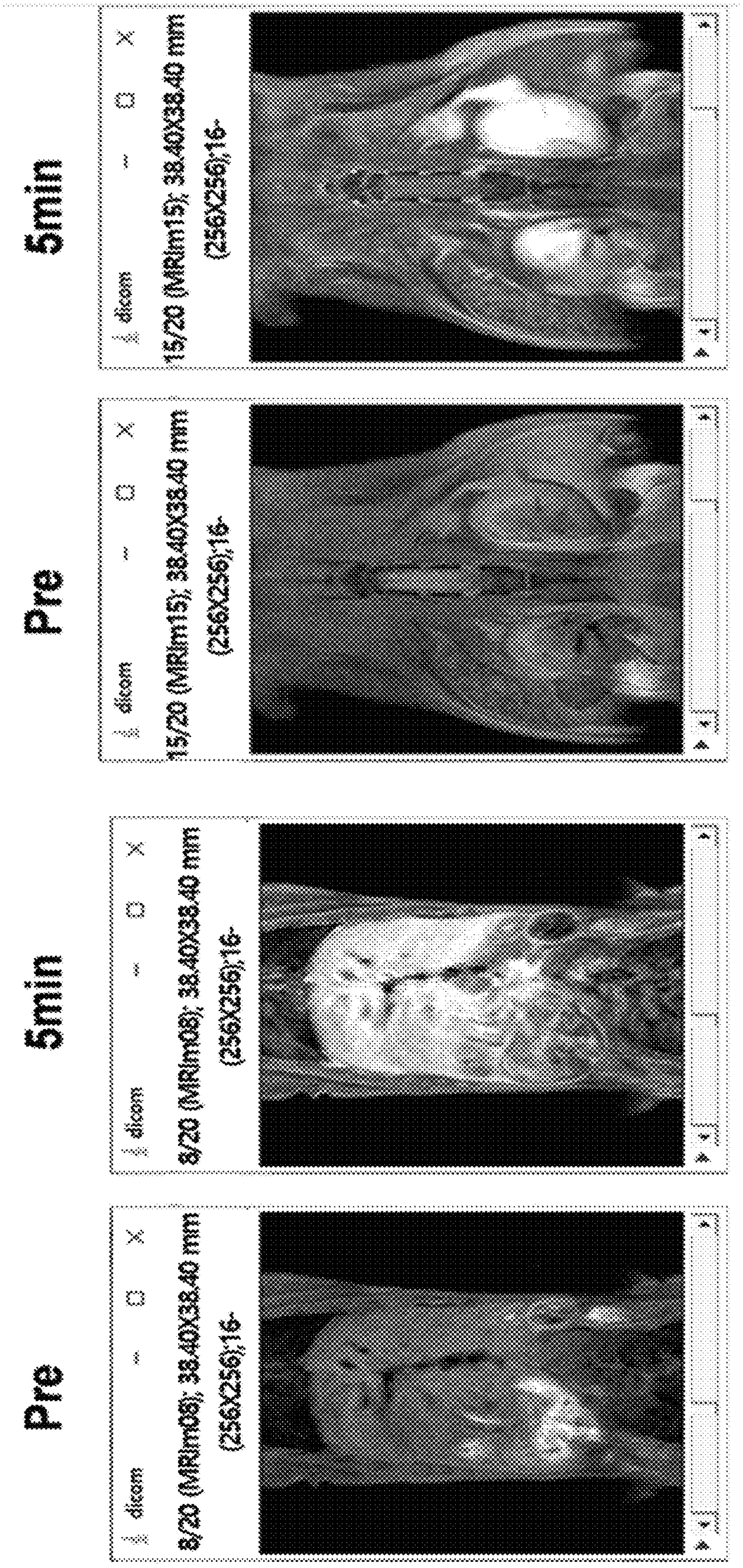
FIG. 15 shows images illustrating the contrast enhancement phenomenon between in vivo $T_1$ MRI within 5 minutes of the (Gd-suc) compound according to Example 1 of the present invention.

Additionally, referring to FIG. 15, Gd-suc showed a very strong contrast enhancement phenomenon in the liver in an in vivo MRI image within 5 minutes, which enables a fast abdominal MRI image from a clinical aspect.

5. In Vitro Cell-Viability Test

Figure 16:
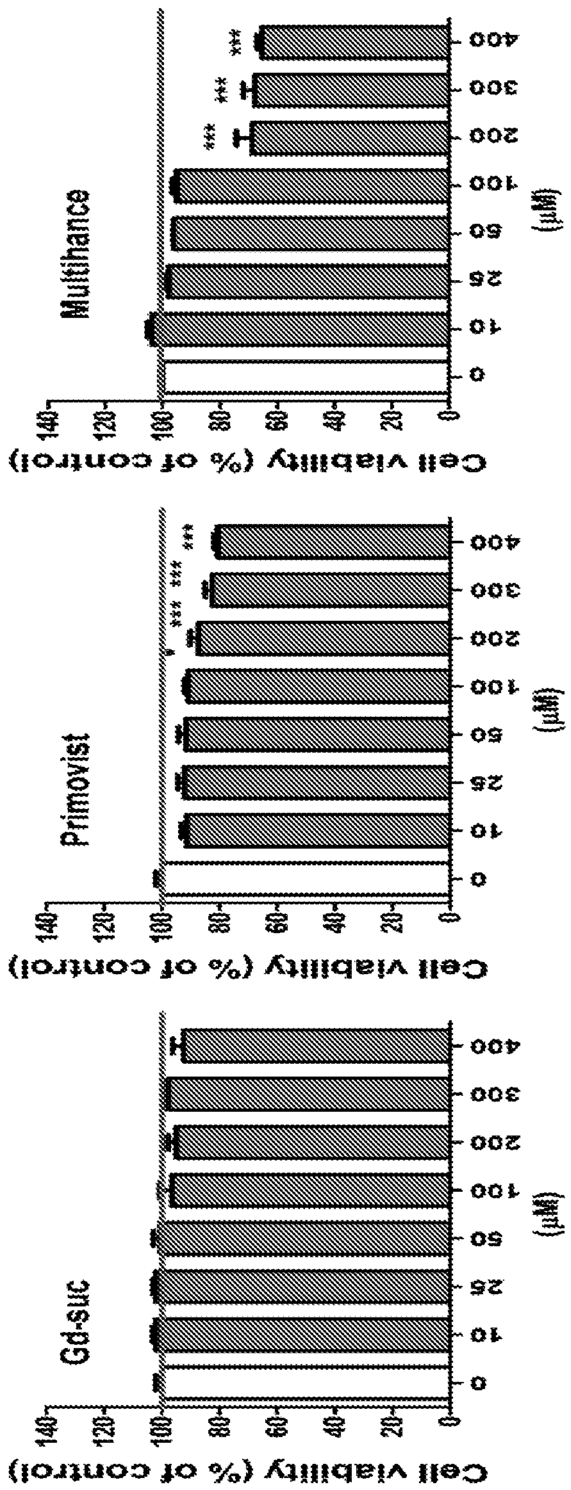
FIG. 16 shows the results of cell viability tests after 24 hours according to the concentrations of the compound (Gd-suc) according to Example 1 of the present invention, Primovist, which is a commercially available liver contrast agent, and Multihance.

In order to confirm the presence or absence of cytotoxicity in normal hepatocytes, Gd-suc (i.e., a compound according to an embodiment of the present invention) and Primovist and Multihance (i.e., commercially available liver contrast agents) were treated on the AML12 cell line at various concentrations, and cell viability after 24 hours was analyzed by a known CCK method, and the results are shown in FIG. 16.

As shown in FIG. 16, Gd-suc (i.e., a compound of the present invention) showed a cell viability of 95% or higher even at a concentration of 400 μM thus indicating no cytotoxicity, whereas Primovist and Multihance (i.e., commercially available liver contrast agents) showed a cell viability of 80% or less at concentrations of 400 μM and 200 μM, respectively, thus indicating significant cytotoxicity.

Although the present invention has been described with reference to preferred embodiments above, it will be understood that those skilled in the art can variously modify and change the present invention without departing from the spirit and scope of the present invention as set forth in the following claims.

The invention claimed is:

1. A compound represented by the following Formula (1):

[Formula 1]

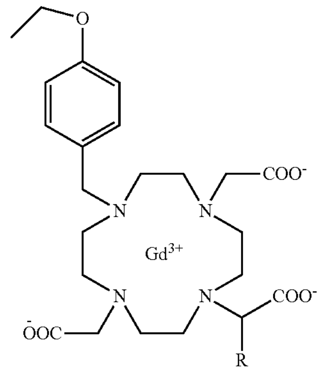

wherein in Formula 1 above,

R represents —COO—, —$CH_2$COO—, or —$CH_2CH_2$COO—.

2. The compound of claim 1, wherein Formula 1 above is represented by the following Formula 1-1:

[Formula 1-1]

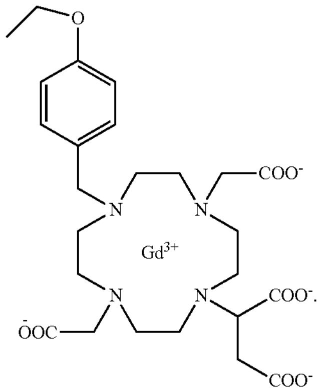

3. The compound of claim 1, wherein Formula 1 above is represented by the following Formula 1-2:

[Formula 1-2]

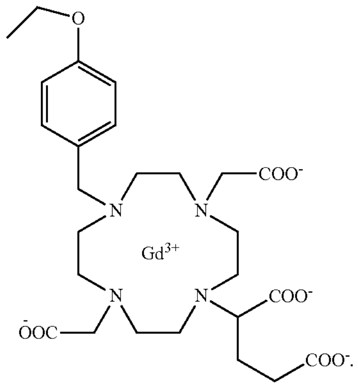

4. The compound of claim 1, wherein Formula 1 above is represented by the following Formula 1-3:

[Formula 1-3]

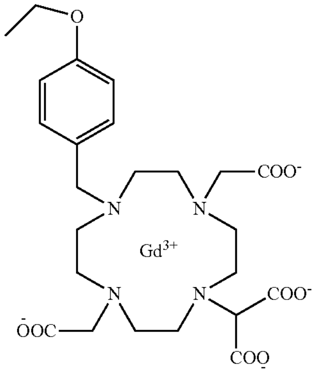

5. The compound of claim 1, wherein the compound specifically binds to liver tissue.

6. An MRI contrast agent containing the compound according to claim 1.

7. The MRI contrast agent of claim 6, wherein the MRI contrast agent is used for the diagnosis of liver diseases.

8. The MRI contrast agent of claim 6, wherein the MRI contrast agent is used for the diagnosis of cancer in liver metastasis, liver cyst, liver cancer, or symptoms of biliary obstruction.

9. The MRI contrast agent of claim 6, wherein the MRI contrast agent has a magnetic relaxation rate of 5 $mM^{-1}s^{-1}$ to 10 $mM^{-1}s^{-1}$ in 4.7 T magnetic resonance imaging.

* * * * *